United States Patent [19]

Luteri

[11] 4,345,933
[45] Aug. 24, 1982

[54] SUCROSE ESTER OF 2-METHOXY-3,6-DICHLOROBENZOIC ACID

[75] Inventor: George F. Luteri, Mt. Prospect, Ill.

[73] Assignee: Velsicol Chemical Corporation, Chicago, Ill.

[21] Appl. No.: 247,471

[22] Filed: Mar. 25, 1981

Related U.S. Application Data

[62] Division of Ser. No. 115,637, Jan. 28, 1980, Pat. No. 4,291,158.

[51] Int. Cl.$^3$ ............... A01N 43/08; A01N 43/16
[52] U.S. Cl. ............................. 71/88; 71/76; 536/119; 536/4; 536/122
[58] Field of Search ............ 536/115, 119; 71/88, 71/107, 76

[56] References Cited

U.S. PATENT DOCUMENTS

| | | | |
|---|---|---|---|
| 3,767,377 | 10/1973 | Poulos | 71/107 |
| 3,862,121 | 1/1975 | Jaques et al. | 536/115 |
| 4,042,538 | 8/1977 | Lucas | 536/115 |

*Primary Examiner*—Blondel Hazel
*Attorney, Agent, or Firm*—Dietmar H. Olesch; Robert J. Schwarz

[57] ABSTRACT

This invention discloses the compound sucrose tri(2-methoxy-3,6-dichlorobenzoate) and its use in a method of increasing the recoverable sugar in sugar cane.

4 Claims, No Drawings

SUCROSE ESTER OF 2-METHOXY-3,6-DICHLOROBENZOIC ACID

This is a division of application Ser. No. 115,637 filed Jan. 28, 1980 now U.S. Pat. No. 4,291,158.

This invention relates to a new composition of matter and more specifically relates to the new chemical compound of the formula

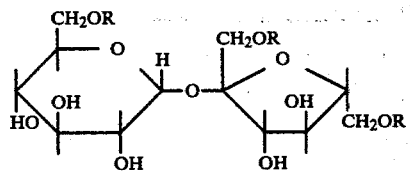

wherein each R is

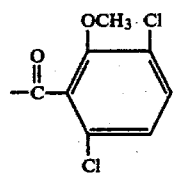

The compound of the foregoing description, hereinafter referred to as sucrose tri(2-methoxy-3,6-dichlorobenzoate), is unexpectedly useful as an agent for increasing the yield of sugar obtained from sugar cane.

The compound of the present invention can be readily prepared by the procedure detailed in the following example.

EXAMPLE 1

Preparation of Sucrose Tri(2-methoxy-3,6-dichlorobenzoate)

Sucrose (34.2 grams; 0.1 mole) and pyridine (300 ml) were charged into a glass reaction vessel equipped with a mechanical stirrer, thermometer and addition funnel. The mixture was stirred and 2-methoxy-3,6-dichlorobenzoyl chloride (71.5 grams; 0.3 mole) was added dropwise at room temperature. After the addition was completed, the reaction mixture was first heated with continued stirring at 75° C. for a period of about 2 hours, followed by heating at 100° C. for a further period of 2 hours. The mixture was then allowed to cool to room temperature and was stirred overnight. After this time the mixture was stripped of pyridine under reduced pressure and the residue was dissolved in ethyl acetate (500 ml). The ethyl acetate solution was then washed with dilute hydrochloric acid, with aqueous sodium chloride (5% conc.) and with water. The washed solution was then dried over anhydrous magnesium sulfate and stripped of solvent to yield the desired product sucrose tri(2-methoxy-3,6-dichlorobenzoate) as a glass.

As previously indicated, the compound of this invention is useful for increasing the yield of sugar in sugar cane. Accordingly, a further embodiment of the present invention resides in a method of increasing the recoverable sugar contained in sugar cane which comprises contacting the sugar cane plant with an effective amount of sucrose tri(2-methoxy-3,6-dichlorobenzoate).

To effect the method of this invention, sugar cane is treated at a late stage of development. This treatment is carried out during that stage of development of the sugar cane wherein most of the sugar formation takes place. Thus, under normal growing conditions and common cultivation practices the active compound of this invention can be applied to the sugar cane during the period of from about 2 to about 10 weeks before harvesting.

The amount of active compound required to effectively increase the recoverable sugar from sugar cane can vary somewhat depending on such factors as the time of application, the weather, crop density, method of application and the like. Generally, an amount of at least 0.1 pounds per acre and preferably an amount of from 0.1 pounds per acre to about 10 pounds per acre can be used. While an amount greater than those mentioned can be used, they will not result in an advantage that would warrant their expense and are therefore, not practical.

For practical use in treating sugar cane, the active compound of this invention is generally incorporated into compositions or formulations which comprise an inert carrier and an effective amount of the compound. The compositions enable the active compound to be conveniently applied to the sugar cane at the desired rate. The formulations can be liquid formulations such as emulsifiable concentrates or solutions or solid formulations such as dusts, granules or wettable powders.

The preferred compositions are liquid formulations, particularly solutions or emulsifiable concentrates. Emulsifiable concentrates comprise the active compound of this invention and as the inert carrier, a solvent and an emulsifier. Such emulsifiable concentrates can be extended with water and/or oil to any desired concentration of active compound for application as sprays to the sugar cane. The emulsifier most commonly used in these concentrates are nonionic or mixtures of nonionic with anionic surface-active agents. With the use of some emulsifier systems, an inverted emulsion (water-in-oil) can be prepared.

Typical formulations according to the present invention useful for increasing the recoverable sugar in sugar cane are illustrated in the following examples wherein the quantities are given in parts by weight.

EXAMPLE 2

Preparation of an Emulsifiable Concentrate

The following ingredients are blended throrougly until homogeneous liquid concentrate is obtained. This concentrate is mixed with water to give an aqueous dispersion containing the desired concentration of the active ingredients for use as a spray.

Product of Example 1—25
Sodium lauryl sulfate—2
Sodium lignin sulfate—3
Aromatic hydrocarbon solvent—70

EXAMPLE 3

Preparation of a Wettable Powder

The following components are mixed intimately in conventional mixing or blending equipment and are then ground to a powder having a particle size of less than about 50 microns. The finished powder is dispersed in water to give the desired concentration of active compound for application to the sugar cane.

Product of Example 1—50
Fuller's earth—47
Sodium lauryl sulfate—2.5

Methyl cellulose—0.5

EXAMPLE 4

Preparation of a Dust

The following ingredients are mixed thoroughly and are then ground to an average particle size of less than about 50 microns to give a dust suitable for application with conventional dusting equipment.

Product of Example 1—10
Powdered talc—90

The effectiveness of the compound of this invention for increasing the recoverable sugar from sugar cane was demonstrated in field tests by applying to sugar cane a solution of the compound in acetone diluted for application to the various indicated application rates. The test compound was applied at each rate on the spindle area of each of 20 stalks of sugar cane in a field in Hawaii, using a syringe with a fine needle as the applicator. A set of 10 of these treated stalks from each group was harvested at 4 and 8 weeks after such treatment. In each harvest a set of 10 untreated stalks were also harvested as a control.

The top 14 joints of the treated cane as well as those of the controls were removed, combined and analyzed for juice purity and pol percent cane, following the "press method" developed and described by T. Tanimoto, Hawaiian Planters Record, 57, 133 (1964). Pol percent cane is a polarimetric determination and equals the percentage of sucrose if the latter is the only substance in the solution which will rotate the plane of polarized light. The pol percent cane is a standard method of determining the sucrose content of sugar cane.

The effectiveness of the compound of this invention for increasing the yield of sugar obtained from sugar cane is demonstrated by the data set out in the following Table. Each test result with accompanying control represents a separate experiment conducted at a different time. The cane was harvested 8 weeks after application of the test compound.

TABLE I

| Rate Lbs./Acre | Juice Purity | Pol % Cane |
|---|---|---|
| 4 | 89.19 | 14.76 |
| Control | 83.90 | 11.07 |
| 1 | 72.93 | 7.77 |
| Control | 77.47 | 9.20 |
| 1 | 79.42 | 10.00 |
| Control | 72.90 | 8.32 |
| 1 | 87.65 | 13.75 |
| Control | 82.76 | 11.81 |

I claim:

1. A method of increasing the recoverable sugar contained in sugar cane which comprises contacting the sugar plant with an effective amount of sucrose tri(2-methoxy-3,6-dichloro-benzoate).

2. The method of claim 1 wherein the sugar cane is contacted with about 0.1 to about 10 pounds per acre of said compound.

3. The method of claim 1 wherein the sugar cane is contacted with said compound during the period of from about 2 to about 10 weeks before harvest.

4. The method of claim 1 wherein the sugar cane is contacted with about 0.1 to about 10 pounds per acre with said compound during the period of from about 2 to about 10 weeks before harvest.

* * * * *